United States Patent
Moisio

(10) Patent No.: US 6,380,749 B1
(45) Date of Patent: Apr. 30, 2002

(54) APPARATUS FOR MEASURING PROPERTIES OF A MOVING PAPER WEB OR CARDBOARD WEB

(75) Inventor: Hannu Moisio, Kangasala (FI)

(73) Assignee: Metso Paper Automation Oy, Tampere (FI)

(*) Notice: Subject to any disclaimer, the term of this patent is extended or adjusted under 35 U.S.C. 154(b) by 0 days.

(21) Appl. No.: 09/622,992
(22) PCT Filed: Feb. 25, 1999
(86) PCT No.: PCT/FI99/00149
§ 371 Date: Aug. 25, 2000
§ 102(e) Date: Aug. 25, 2000
(87) PCT Pub. No.: WO99/44008
PCT Pub. Date: Sep. 2, 1999

(30) Foreign Application Priority Data

Feb. 26, 1998 (FI) .................................................. 980443

(51) Int. Cl.[7] ................................................. H01F 5/00
(52) U.S. Cl. ........................ 324/654; 336/200; 336/232
(58) Field of Search ............................... 324/229, 230, 324/231, 234, 236, 241, 239, 654; 336/200, 232; 493/3, 26; 226/45

(56) References Cited

U.S. PATENT DOCUMENTS

| | | | |
|---|---|---|---|
| 3,772,587 A | * 11/1973 | Farrand et al. ............... | 336/10 |
| 4,107,606 A | 8/1978 | Typpo et al. | |
| 4,292,838 A | * 10/1981 | Larsen ....................... | 73/37.7 |
| 4,528,507 A | 7/1985 | Domin et al. | |
| 4,791,367 A | 12/1988 | Typpo | |
| 5,245,307 A | * 9/1993 | Klaus et al. ................ | 336/200 |
| 5,414,402 A | * 5/1995 | Mandai et al. .............. | 336/200 |
| 5,418,823 A | 5/1995 | Kervinen et al. | |
| 5,453,689 A | * 9/1995 | Goldfine et al. ............ | 324/239 |
| 5,659,248 A | 8/1997 | Hedengren et al. | |
| 5,801,521 A | * 9/1998 | Mizoguchi et al. ......... | 323/282 |

FOREIGN PATENT DOCUMENTS

EP 0 687 907 A1 12/1995
GB 2 321 787 A 8/1998

OTHER PUBLICATIONS

PCT International Search Report, PCT/FI99/00149, completed on Jul. 13, 1999.
Copy of Finnish Official Action, Appl. No. 980443, dated Nov. 23, 1998.

* cited by examiner

Primary Examiner—Safet Metjahic
Assistant Examiner—Vincent Q. Nguyen
(74) Attorney, Agent, or Firm—Alston & Bird LLP

(57) ABSTRACT

The invention relates to an apparatus for measuring properties of a moving paper web or cardboard web. The apparatus comprises a sensor and a counterpart. The sensor comprises at least one coil. The sensor is arranged on a first side of the moving web and the counterpart is arranged on a second side of the moving web. The coil comprises a plurality of layers, each layer constituting a part of the coil, the layers being superimposed and coupled in series to constitute the coil.

12 Claims, 1 Drawing Sheet

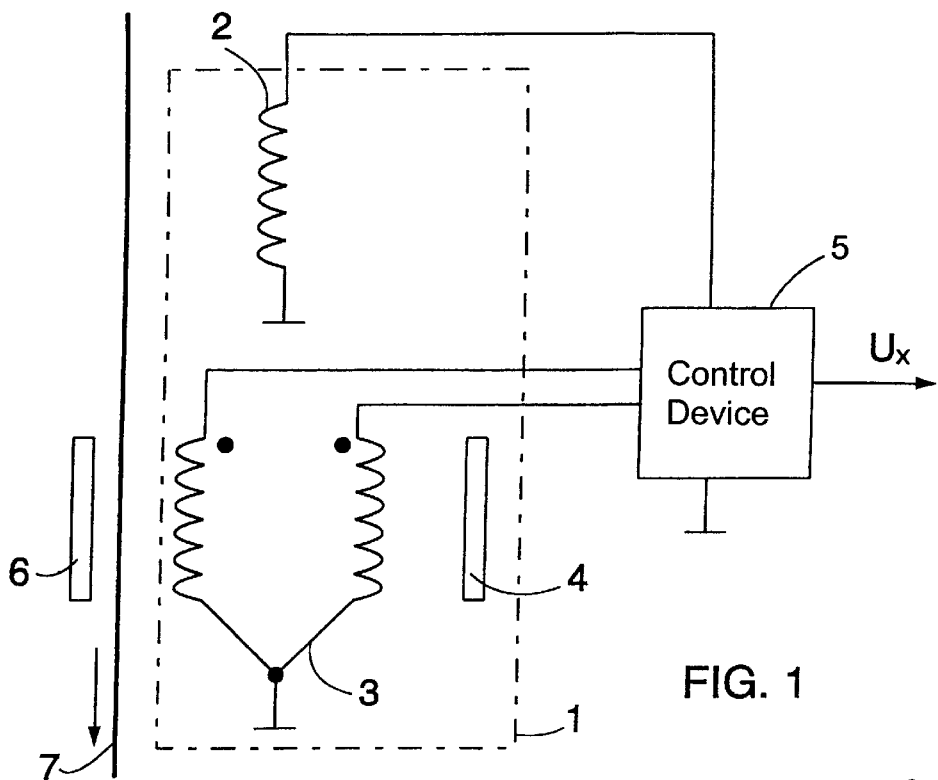
FIG. 1
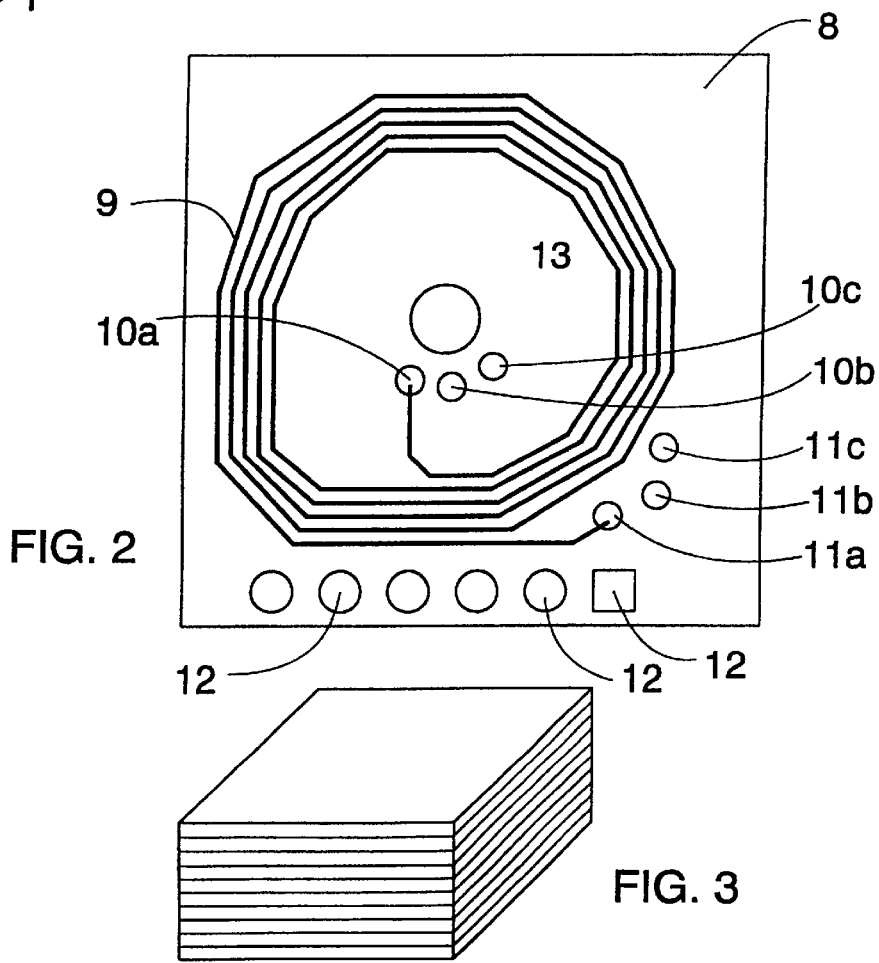
FIG. 2
FIG. 3

APPARATUS FOR MEASURING PROPERTIES OF A MOVING PAPER WEB OR CARDBOARD WEB

FIELD OF THE INVENTION

The invention relates to an apparatus for measuring properties of a moving paper web or cardboard web the apparatus comprising a sensor and a counterpart, the sensor being arranged on a first side of the web and the counterpart on a second side of the web, the sensor comprising at least one coil.

BACKGROUND OF THE INVENTION

Measurements of properties of a moving paper web constitute the basis for controlling a paper machine. Continuous monitoring of properties: e.g. the caliper of paper, as the web moves, ensures that paper of the right quality is produced. The problem in measuring the caliper of a moving web is that the web moves at an extremely high speed and that the web always comprises some discontinuities, such as holes and small bulges. Measuring sensors located very near the surface of the web, or even in contact with it, should be able to give way to the discontinuities in order for the measurement to be reliable and the sensors not to cause additional hole formation. Present devices are not capable of giving way sufficiently rapidly, and consequently formation of holes has been prevented e.g. by keeping sensors far away from the web. This impairs measuring results.

U.S. Pat. No. 4,791,367 discloses a gauge for measuring the caliper of a web. The gauge comprises an upper head having a U-shaped magnetic pole piece whose legs are provided with windings. A lower head to be arranged on the opposite side of the paper web to be measured comprises a passive magnetic circuit which is a magnetic or ferrite plate. The magnetic flux established by the windings extends through the pole piece through the paper to the ferrite plate. The gap between the pole piece and the ferrite plate varies as the caliper of the paper web varies. The circuit inductance used to define the caliper of the paper web also varies simultaneously.

U.S. Pat. No. 4,528,507 discloses a solution for measuring properties of a moving web by sensors arranged on different sides of the web. One of the sensors is provided with a coil, the sensor on the opposite side of the web being provided with a counterplate. As the gap between the coil and the counterplate varies, the density of the magnetic flux established by the coil varies and the caliper of the web is measured by detecting the variation in the density.

German Offenlegungsschrift 28 29 264 discloses a measuring apparatus, in which a sensor including a coil is arranged on both sides of the web. The caliper of the web is measured by defining the amplitude of the magnetic field established by the coils.

In all the above solutions, the sensor coils, typically made from copper wire, are heavy, making the sensors heavy and difficult to move flexibly along formations on the surface of paper. Furthermore, because the construction is heavy, the sensors are also very poorly adapted to float by air bearings, completely clear of the surface of paper.

It is an object of the present invention to provide an apparatus for avoiding the above drawbacks.

SUMMARY OF THE INVENTION

The apparatus of the invention is characterized in that the coil comprises a plurality of layers, each layer constituting a part of the coil, the layers being superimposed and coupled in series to constitute the coil.

It is an essential idea of the invention that the apparatus for measuring properties of a paper web comprises at least one coil comprising a plurality of coil parts arranged as superimposed layers and coupled in series at their ends to form an integral coil. It is the idea of a preferred embodiment that the injection frequency used in the solution exceeds 50 kHz.

It is an advantage of the invention that the sensors of the measuring apparatus of the invention can be made lightweight, whereby the sensors are able to give way to irregularities on the surface of the paper more flexibly than before. This decreases formation of holes in the paper. The lightweight construction of the invention also allows the sensors to be made such that they float by means of air bearing. The construction can be made lightweight, since, owing to the high injection frequency, the measuring apparatus requires no heavy ferromagnetic materials, such as iron, ferrite or a large conductor coil made from copper wire. In the solution of the invention the number of wire turns of the coils can be low, resulting in a small and lightweight measuring apparatus.

BRIEF DESCRIPTION OF THE FIGURES

The invention will be described in greater detail in the attached drawing, wherein FIG. 1 schematically shows an apparatus of the invention, FIG. 2 schematically shows one layer of a coil structure to be used in the apparatus of FIG. 1, and FIG. 3 schematically shows a coil structure to be used in the apparatus of FIG. 1.

DETAILED DESCRIPTION OF THE PREFERRED EMBODIMENTS

FIG. 1 shows a measuring sensor 1 comprising a feed coil 2, a differential coil 3 comprising two coils, and a reference plate 4. The measuring apparatus further comprises a control device 5 for feeding control current to the feed coil 2. The injection frequency of the feed coil is advantageously high. i.e. above 50 kHz, preferably above 200 kHz. Typically the injection frequency is about 250 kHz, but may be even 500 kHz or more. If the injection frequency is high, the number of wire turns of the coils 2 and 3 can be low, resulting in a small and lightweight measuring sensor.

The feed coil 2 induces to the differential coil circuit a voltage which can be measured by the control device 5 by e.g. lock-in type of detection. The reference plate 4 is arranged on one side of the differential coil. The gap between the differential coil 3 and the reference plate 4 is substantially constant at all times. A sensor plate 6 is arranged on the side of the differential coil 3 which is opposite with regard to the reference plate 4. The structures of the reference plate 4 and the sensor plate 6 are substantially identical. The plates are made from a material which efficiently conducts electricity, e.g. copper. The plate can also comprise merely a conductive metal surface produced by vaporizing. When the material effectively conducts electricity, a thin conductive layer is sufficient. A thin conductive layer is sufficient because the higher the injection frequency, the smaller is the current penetration depth inside the conducting body. Furthermore, owing to a high injection frequency, the plates 4 and 6 can be made thin and consequently their masses can be kept small.

The measuring sensor 1 is placed on a first side of a web 7 and the sensor plate 6 to a second side of the web 7, i.e.

the opposite side with regard to the measuring sensor 1. The web 7 is a moving web and can be e.g. a paper or cardboard web, whose caliper is to be measured. The measuring sensor 1 and the sensor plate 6 are arranged either in contact with the web 7 or close to the surface of the web 7 e.g. by means of an air bearing. As the caliper of the web 7 varies, the distance between the sensor plate 6 and the measuring sensor 1 and, naturally, the differential coil 3 and the reference plate 4, varies. This variation in distance caused by the caliper of the web 7 affects the voltage of the differential coil 3 to be detected by means of the control device 5. Accordingly, the control device 5 produces a voltage Ux, which is proportional to the distance between the differential coil 3 and the sensor plate 6, i.e. the caliper of the web 7.

The coils 2 and 3 comprise a plurality of coil parts arranged as superimposed perimeter layers. FIG. 2 shows one such layer. The layer of FIG. 2 has been formed e.g. by exposing a copper-coated circuit board 8, except for the location of the conductor 9, and by then corroding the removed copper in such a way that only a spiral copper conductor 9 remains on top of the circuit board 8. The conductor spiral 9 begins by an inner opening 10*a* and ends in an outer opening 11*a*. The end of the conductor 9 is connected via the inner opening 10*a* to the conductor of the layer underneath, the latter conductor providing the layer underneath with a spiral of substantially the same shape but unwinding in a different direction, the conductors 9 of the different layers, however, winding in the same direction. The conductor 9 end which ends in the outer opening 11*a* is connected to the end of the conductor 9 of the upper layer by through coppering. The conductor spiral 9 in the upper layer also winds in an opposite direction with respect to the spiral in FIG. 2, whereby the directions of winding of the conductors remain the same. The circuit board of FIG. 2 also comprises other inner openings 10*b* and 10*c* and outer openings 11*b* and 11*c*, which can be utilized in combining the conductors of layers on the lower or upper side of a circuit board according to FIG. 2.

The circuit board 8 is further provided with connectors 12 for connecting a coil construction comprising superimposed circuit boards to a measuring apparatus. The circuit board 8 is further provided substantially in the middle with an axis opening 13 by means of which the circuit boards 8 to be superimposed can be aligned. The pattern formed by the conductor 9 is most preferably as round and symmetric as possible. If required, the symmetric construction can be slightly deviated from according to the disposition of the inner openings 10*a* to 10*c* and the outer openings 11*a* to 11*c* required in the different layers, as is the case in the lower left edge of the conductor spiral 9 in FIG. 2.

FIG. 3 shows a coil construction with circuit boards 8 according to FIG. 2 being superimposed to form a coil. About 30 layers, for example, can be superimposed and yet the resulting coil construction is only a few millimeters high. A conductor 9 substantially according to FIG. 2 can be provided both below and above the circuit board 8, an insulating layer being arranged between the circuit boards 8 to be superimposed. In the coil construction of FIG. 3. the direction of winding of the conductor 9 can be changed e.g. in the middle part of the construction in order to achieve a differential coil 3 according to FIG. 1. Naturally the point where the direction of winding changes can easily be combined with a connector 12. The coils can be manufactured mechanically in series production, resulting in the significant advantage that the coils are identical irrespective of production lot.

The drawings and the related description are only intended to illustrate the inventive idea. The details of the invention may vary within the scope of the claims. Consequently, the one layer forming a part of the coil can be made e.g. by the printed circuit technique or by arousing the conductor electrolytically or by vaporization or by some other corresponding manner.

The feed coil is not necessary, and electric current may also be fed directly to a part of the differential coil 3. In this case said part of the differential coil 3 would serve as the feed coil 2. Furthermore, the structure of the differential coil 3 may comprise more than two coils. The differential coil 3 is most preferably symmetric, whereby the voltage Ux produced by the control device 5 is close to zero at least in e.g. caliper measurements involving thinner qualities.

What is claimed is:

1. An apparatus for measuring properties of a moving paper or cardboard web, the apparatus conspiring:
    a sensor and a counterpart, the sensor being arranged on a first side of the web and the counterpart an a second side of the web; and
    an air bearing connected to said sensor for floating said sensor above the web,
        wherein said sensor comprises at least one coil that comprises a plurality of layers, each layer constituting a part of the coil and being superimposed and coupled in series to constitute the coil, wherein the layered coil is less in weight than a corresponding coil made from wire, such that the sensor is more easily floated above the web by said air bearing.

2. An apparatus as claimed in claim 1 wherein the layer constituting a part of the coil is formed on a circuit board by providing the circuit board with a spiral-shaped conductor.

3. An apparatus as claimed in claim 1 wherein the sensor and counterpart are structured to measure at least the caliper of a paper or cardboard web.

4. An apparatus for measuring properties of a moving paper or cardboard web, the apparatus comprising:
    a sensor and a counterpart, the sensor being arranged on a first side of the web and the counterpart on a second side of the web,
        the sensor comprising at least one coil that comprises a plurality of layers, each layer constituting a part of the coil and being superimposed and coupled in series to constitute the coil; and
    a control device in electrical communication with said sensor, wherein said control device provides an injection frequency exceeding 50 KHz, wherein use of injection frequencies exceeding 50 KHz by said control device reduces the number of layers required in said coil thereby decreasing the weight of said coil such that the sensor is more easily floated above the web by said air bearing.

5. An apparatus for measuring properties of a moving paper or cardboard web, the apparatus comprising:
    a sensor and a counterpart, the sensor being arranged on a first side of the web and the counterpart on a second side of the web,
        wherein the sensor comprises:

at least one coil that comprises a plurality of layers, each layer constituting a part of the coil and being superimposed and coupled in series to constitute the coil;

a differential coil comprising at least two coils and a reference plate, and wherein the counterpart is a sensor plate that is substantially similar to the reference plate.

6. An apparatus as claimed in claim 5 wherein the sensor further comprises a feed coil for feeding electric current to the differential coil.

7. A sensor for use in measuring properties of a moving paper or cardboard web, the sensor comprising:

at least one coil that is arranged adjacent a surface of the moving web, said coil comprising, a plurality of layers, each layer constituting a part of the coil and being superimposed and coupled in series to constitute the coil, wherein the layered coil is less in weight than a corresponding coil made from wire, such that the sensor is more easily floated above the web by an air bearing.

8. A sensor as claimed in claim 7 wherein the layer constituting a part of the coil is formed on a circuit board by providing the circuit board with a spiral-shaped conductor.

9. A sensor as claimed in claim 7 wherein said sensor operates with an injection frequency that exceeds 50 KHz.

10. A sensor as claimed in claim 7 wherein the sensor is structured to measure at least the caliper of a paper or cardboard web.

11. A sensor for use in measuring properties of a moving paper or cardboard web, the sensor comprising:

at least one coil that is arranged adjacent a surface of the moving web, said coil comprising a plurality of layers, each layer constituting a part of the coil and being superimposed and coupled in series to constitute the coil; and a differential coil comprising at least two coils and a reference plate.

12. A sensor as claimed in claim 11 wherein the sensor further comprises a feed coil for feeding electric current to the differential coil.

* * * * *

UNITED STATES PATENT AND TRADEMARK OFFICE
CERTIFICATE OF CORRECTION

PATENT NO. : 6,380,749 B1
DATED : April 30, 2002
INVENTOR(S) : Moisio

It is certified that error appears in the above-identified patent and that said Letters Patent is hereby corrected as shown below:

Column 4,
Line 25, "conspiring" should read -- comprising --;
Line 27, "an" should read -- on --.

Signed and Sealed this

Sixteenth Day of July, 2002

Attest:

Attesting Officer

JAMES E. ROGAN
Director of the United States Patent and Trademark Office